United States Patent

Huff et al.

[11] Patent Number: 5,807,841
[45] Date of Patent: Sep. 15, 1998

[54] HIV PROTEASE INHIBITORS USEFUL FOR THE TREATMENT OF AIDS

[75] Inventors: Joel R. Huff, Gwynedd Valley; Joseph P. Vacca, Telford; Bruce D. Dorsey, Harleysville, all of Pa.

[73] Assignee: Merck & Co., Inc., Rahway, N.J.

[21] Appl. No.: 825,787

[22] Filed: Apr. 8, 1997

Related U.S. Application Data

[62] Division of Ser. No. 412,509, Mar. 29, 1995, Pat. No. 5,646,148, which is a continuation of Ser. No. 170,475, Dec. 20, 1993, abandoned, which is a continuation-in-part of Ser. No. 168,013, Dec. 15, 1993, abandoned.

[51] Int. Cl.$^6$ .................. A61K 31/70; A61K 31/495; A61K 31/50
[52] U.S. Cl. .................. 514/45; 514/49; 514/50; 514/253
[58] Field of Search .................. 514/45, 49, 50, 514/253

[56] References Cited

U.S. PATENT DOCUMENTS 5,413,999  5/1995  Vacca et al. .................. 514/231.5
5,502,060  3/1996  Thompson et al. .................. 514/307

FOREIGN PATENT DOCUMENTS 0337714  10/1989  European Pat. Off. .
0541168  12/1993  European Pat. Off. .

*Primary Examiner*—Jerome D. Goldberg
*Attorney, Agent, or Firm*—Kenneth R. Walton; Melvin Winokur

[57] ABSTRACT

Compounds of formula

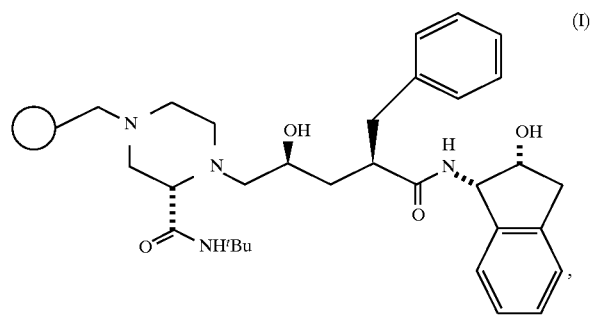

are HIV protease inhibitors. These compounds are useful in the prevention or treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS and methods of preventing or treating infection by HIV are also described.

3 Claims, No Drawings

HIV PROTEASE INHIBITORS USEFUL FOR THE TREATMENT OF AIDS

This application is a divisional of U.S. Ser. No. 08/412,509, filed Mar. 29, 1995, now U.S. Pat. No. 5,646,148, which is a continuation application of U.S. Ser. No. 08/170,475, filed Dec. 20, 1993, now abandoned, which is a continuation-in-part application of 08/168,013, filed Dec. 15, 1993, now abandoned.

The present invention is concerned with compounds which inhibit the protease encoded by human immunodeficiency virus (HIV), or pharmaceutically acceptable salts thereof, and are useful in the prevention of infection by HIV, the treatment of infection by HIV and the treatment of the resulting acquired immune deficiency syndrome (AIDS). It also relates to pharmaceutical compositions containing the compounds and to a method of use of the present compounds and other agents for the treatment of AIDS and viral infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., Proc. Nat'l Acad. Sci. 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., Nature, 313, 277(1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)]. Applicants demonstrate that compounds of this invention are inhibitors of HIV protease.

BRIEF DESCRIPTION OF THE INVENTION

Compounds of formula I, as herein defined, are useful in the inhibition of HIV protease, the prevention of infection by HIV, the treatment of infection by HIV and in the treatment of AIDS, either as compounds, pharmaceutically acceptable salts, pharmaceutical composition ingredients, whether or not in combination with other antivirals, immunomodulators, antibiotics or vaccines. Methods of treating AIDS, methods of preventing infection by HIV, and methods of treating infection by HIV are also disclosed.

Some abbreviations that may appear in this application are as follows.

| ABBREVIATIONS | |
|---|---|
| Designation | |
| | Protecting Group |
| BOC (Boc) | t-butyloxycarbonyl |
| CBZ (Cbz) | benzyloxycarbonyl(carbobenzoxy) |
| TBS (TBDMS) | t-butyl-dimethylsilyl |
| | Activating Group |
| HBT(HOBT or HOBt) | 1-hydroxybenzotriazole hydrate |
| Designation | Coupling Reagent |
| BOP reagent | benzotriazol-1-yloxytris-(dimethylamino)phosphonium hexafluorophosphate |
| BOP-Cl | bis(2-oxo-3-oxazolidinyl)phosphinic chloride |
| EDC | 1-ethyl-3-(3-dimethylaminopropyl) carbodiimide hydrochloride |
| | Other |
| $(BOC)_2O$ $(BOC_2O)$ | di-t-butyl dicarbonate |
| $n-Bu_4N+F-$ | tetrabutyl ammonium fluoride |
| nBuLi (n-Buli) | n-butyllithium |
| DMF | dimethylformamide |
| $Et_3N$ | triethylamine |
| EtOAc | ethyl acetate |
| TFA | trifluoroacetic acid |
| DMAP | dimethylaminopyridine |
| DME | dimethoxyethane |
| LDA | lithium diisopropylamide |
| THF | tetrahydrofuran |

DETAILED DESCRIPTION OF THE INVENTION AND PREFERRED EMBODIMENTS

This invention is concerned with compounds of formula I, combinations thereof, or pharmaceutically acceptable salts thereof, in the inhibition of HIV protease, the prevention or treatment of infection by HIV and in the treatment of the resulting acquired immune deficiency syndrome (AIDS). Compounds of formula I are defined as follows:

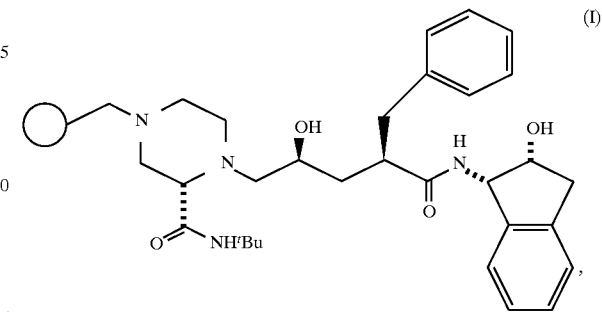

or a pharmaceutically acceptable salt thereof, wherein:

is a stable 8- to 10-membered bicyclic heterocycle, any ring of which may be saturated or unsaturated, and said heterocycle consists of carbon atoms and 1–3 heteroatoms selected from the group consisting of N, S or O, said heterocycle being unsubstituted or substituted with OH, halo, $C_{1-4}$ alkyl, oxo;

with the proviso that

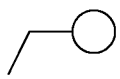

is neither

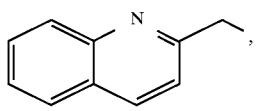

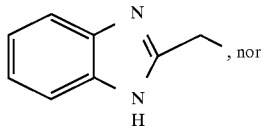, nor

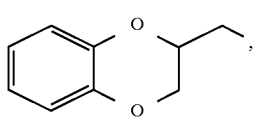

One embodiment of the present invention is compounds of formula I, or a pharmaceutically acceptable salt thereof, wherein:

is a stable 8- to 10-membered bicyclic heterocycle, any ring of which may be saturated or unsaturated, and said heterocycle consists of carbon atoms and 2 heteroatoms selected from the group consisting of N or O, wherein the heteroatoms are in different rings.

A second embodiment are compounds of formula I wherein:

is restricted to

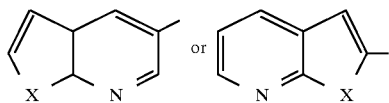

and X is O or S, or a pharmaceutically acceptable salt thereof.

A third embodiment are compounds of formula I wherein:

is restricted to

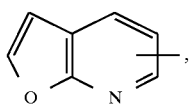

or pharmaceutically acceptable salts thereof

Another embodiment of the present invention is compound A:

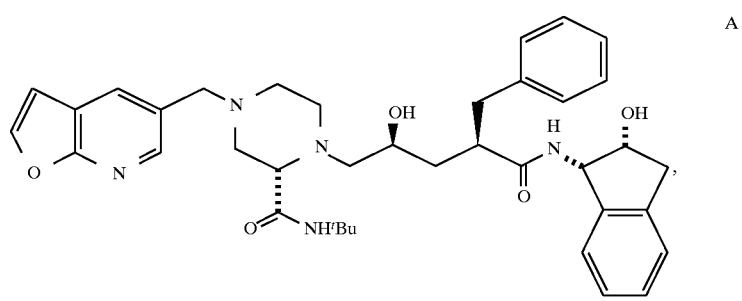

A which is N-(2(R)-hydroxy-1(S)-indanyl)-2(R)-phenylmethyl-4(S)-hydroxy-5-(1-(4-(3-furo[2,3-b]pyridylmethyl)-2(S)-N'-(t-butylcarbox-amido)-piperazinyl))pentaneamide, or pharmaceutically acceptable salt thereof.

The compounds of the present invention, have chiral centers and occur as racemates, racemic mixtures and as individual diastereomers, or enantiomers with all isomeric forms being included in the present invention. A racemic mixture encompasses mixtures of stereoisomers of 50:50 and other ratios.

When any variable (e.g.,

)

occurs more than one time in any constituent or in formula I, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "Halo", as used herein, means fluoro, chloro, bromo and iodo.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dihydrochloride, diphosphate, dodecylsulfate, ethanesulfonate, fumarate, glucoheptanoate, glutamate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, phosphate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Other pharmaceutically acceptable salts include the sulfate salt ethanolate and sulfate salts.

Schemes I–II for preparing the novel compounds of this invention are presented below. The examples specifically illustrate the application of the following schemes to specific compounds.

Amide couplings used to form the compounds of this invention are typically performed by the carbodiimide method with reagents such as dicyclohexylcarbodiimide, or 1-ethyl-3-(3-dimethyl-aminopropyl) carbodiimide. Other methods of forming the amide or peptide bond include, but are not limited to the synthetic routes via an acid chloride, azide, mixed anhydride or activated ester. Typically, solution phase amide coupling are performed, but solid-phase synthesis by classical Merrifield techniques may be employed instead. The addition and removal of one or more protecting groups is also typical practice.

Additional related information on synthetic background is contained in EPO 0337714 and EPO 0541168.

One method for producing formula I compounds is provided by Scheme I. Dihydro-5(S)-(tert-butyldimethylsilyloxy-methyl)-3(2H)-furanone (compound 1 below) is prepared by standard methods known in the art from commercially available dihydro-5(S)-(hydroxymethyl)-2(3H)-furanone. After alkylation of compound 1 to form compound 2, the protecting group of lactone 2 is removed with aqueous HF to afford compound 3.

The alcohol group of 3 is activated by conversion into a leaving group such as mesylate, tosylate or triflate by treating the alcohol with a sulfonyl chloride or (preferably) sulfonic anhydride, such as trifluoromethanesulfonic anhydride, in the presence of a hindered amine base such as triethylamine, diethyl isopropylamine or 2,6 lutidine, to afford a compound such as compound 4. The leaving group of compound 4 is displaced by an amine 5, such as 4-(1,1-dimethyl ethoxycarbonylamino)-piperazine-2(S)-carboxamide in a solvent such as DMF or xylene to produce a compound such as 6. A trifluoromethanesulfonyloxy group can be displaced by an amine at room temperature in a solvent such as isopropanol or methylene chloride by treatment with N,N-diisopropyl-ethylamine.

Compound 6 is hydrolyzed with aqueous lithium or sodium hydroxide and the resultant hydroxy acid 7 is converted into a protected hydroxy acid 8. The hydroxyl group is conveniently protected with a standard silyl protecting group such as t-butyldimethyl silyl or t-butyldiphenyl silyl.

The protected hydroxy-acid 8 is then coupled to the desired $R^{12}$ amine to produce compound 9, and the silyl protecting group is removed with fluoride ion to arrive at compound 10.

SCHEME I

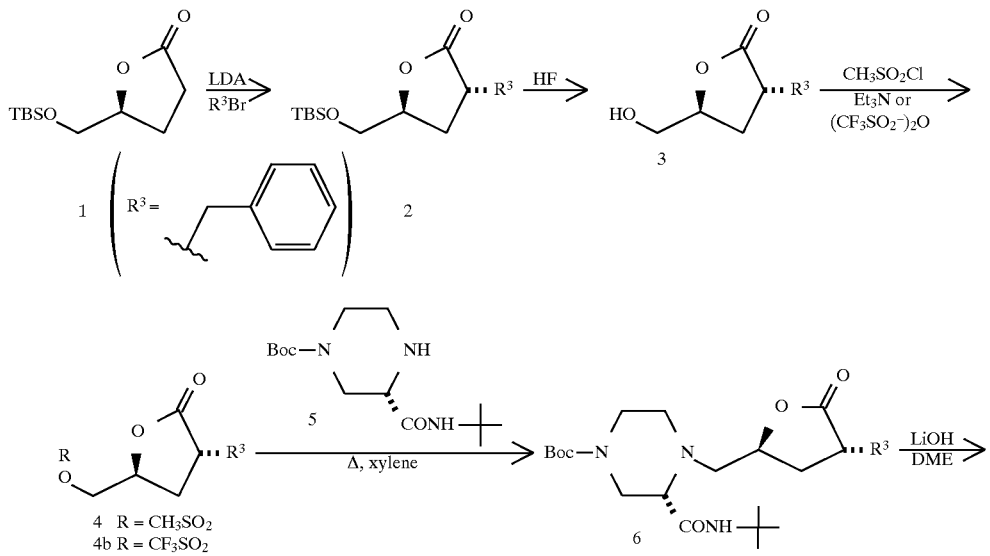

-continued
SCHEME I

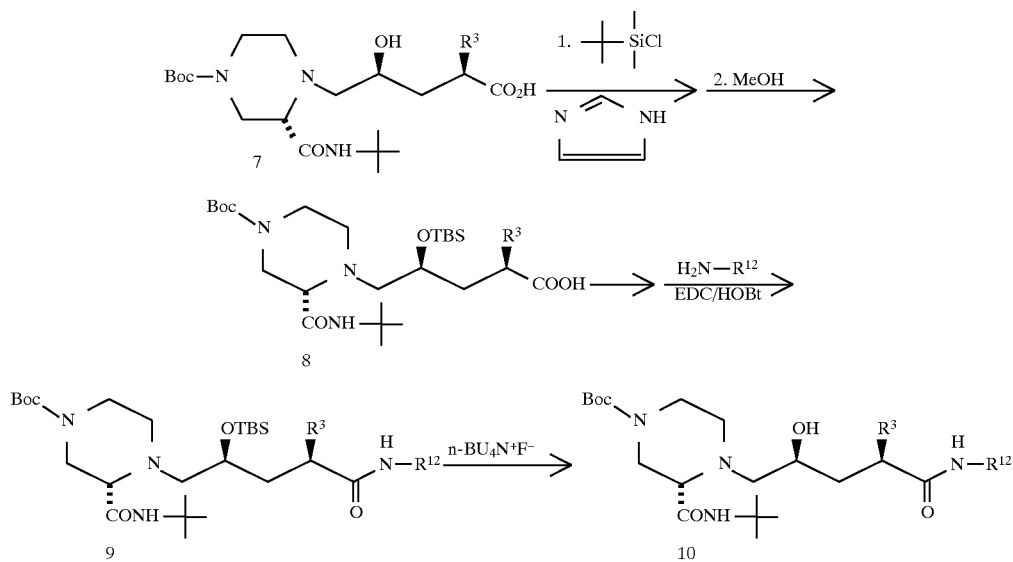

SCHEME II

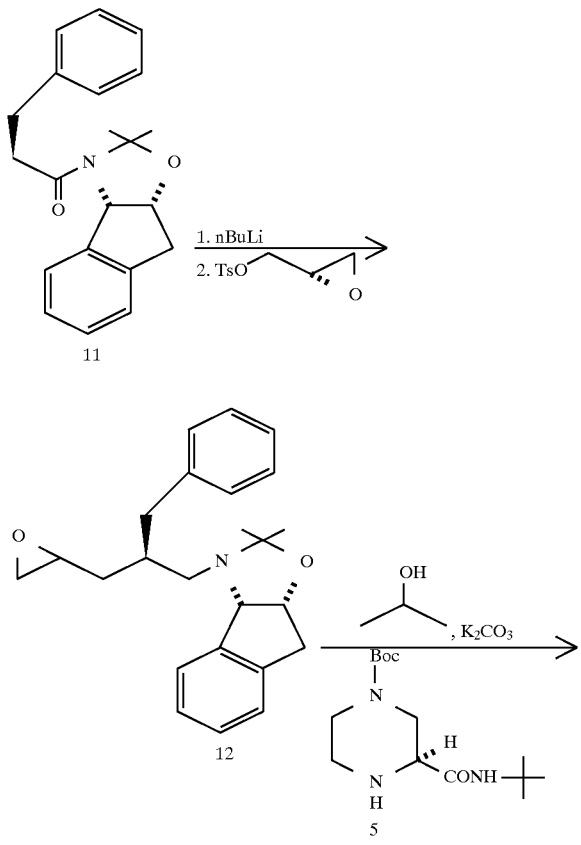

-continued
SCHEME II

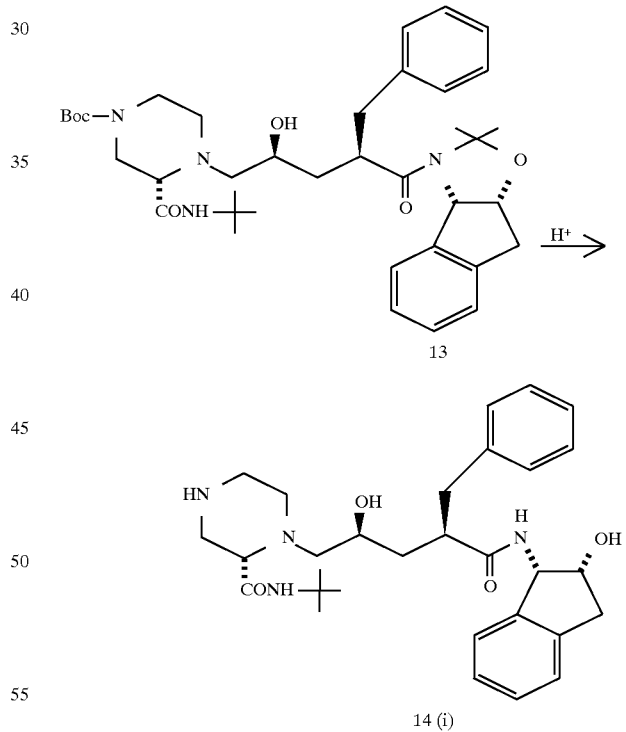

One preferred method is the synthesis of the epoxide 12 by reaction of 11 in the presence of strong base. The strong base must be a metal-containing base, in an inert anhydrous organic solvent, such as, e.g., cyclic or acyclic hydrocarbons including hexane, pentane, cyclohexane, etc. Suitable strong bases include: $LiN[(CH_3)_3Si]_2$, $KN[(CH_3)_3Si]_2$, $NaN[(CH_3)_3Si]_2$, n-butyllithium (n-BuLi), s-BuLi, t-BuLi, potassium tert-butoxide, lithium diisopropyl-amide (LDA), lithium isopropylcyclohexylamide, lithium pyrrolidide, lithium tetramethylpiperidide, phenyllithium, isopropylmagnesium chloride, isobutylmagensium chloride, and other similar strong base known in the art. Preferred strong bases are n-BuLi, s-BuLi, LiN[(CH$_3$)$_3$Si]$_2$ and LDA, with n-BuLi and LiN[(CH$_3$)$_3$Si]$_2$ being most preferred. Preferably, about 1 to 2 molar equivalents of strong base are used per 1 molar equivalent of 11.

Compound 13 is made by reacting compound 12 with N-t-butyl-4-(1,1-dimethylethoxycarbonylamino)piperazine-2(S)-carboxamide (5). Preferably from about 1 to 3 molar equivalents of amine 5 are used per molar equivalent of epoxide 12, with a ratio of about 1.05:1 molar equivalents of V:IV being more preferred.

This reaction can be run in any suitable solvent, such as, e.g., one chosen from hydrocarbons, such as toluene, ethers such as di-ethyl ether, alcohols such as methanol, ethanol or isopropanol, nitrites such as acetonitrile, and esters such as ethyl acetate or combinations thereof, with alcohols being preferred and isopropanol being most preferred. The temperature of the reaction can be maintained in a range from ambient to the reflux temperature of the solvent used, but is preferably run at an elevated temperature, e.g., in the range of 80° C. to 90° C., and most preferably from about 83° C. to 85° C.

Activated glycidols can be prepared by methods known in the art, such as described in, e.g., J. Klunder, et al., *J. Org. Chem.*, 1989, 54, 1295–1304 and references cited therein.

Amide compounds such as 11 can be made according to standard procedures known to those skilled in the art, such as, e.g., the procedure described in Example 10, using the appropriate starting materials.

Protecting groups such as nitrogen protecting groups may be used where appropriate in the practice of this invention. For example, the 4 position nitrogen of 2-t-butylcarboxamide piperazine may be protected with a group such as BOC, CBZ, benzyl, 4-methoxybenzyl, 2,4-dimethoxybenzyl, trifluoroacetamide, trialkylsilyl, or other groups known in the art.

A compound of formula 15

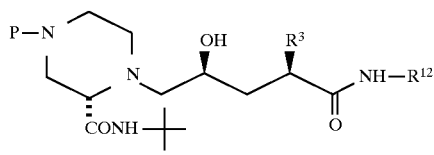

15 wherein P is a nitrogen protecting group such as —BOC or —CBZ, is also prepared according to the method described in Scheme I, preferably employing the 5-trifluoromethanesulfonyloxymethyl analog of lactone 4 therein.

Compounds of formula 16

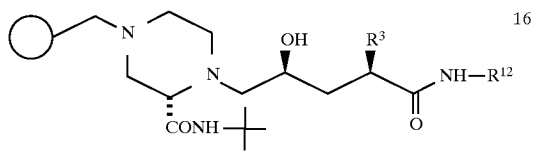

16 can be obtained by a variety of routes from compound 14

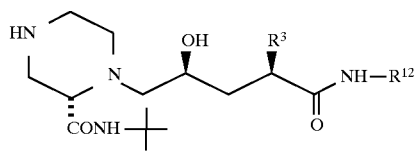

14 which is obtained after removal of the nitrogen protecting group in 15 using methods well known in the art, e.g., catalytic hydrogenation to remove a CBZ group, or treatment with trimethylsilyltriflate and 2,6 lutidine at about 0° C. in a solvent such as CH$_2$Cl$_2$, or treatment with 6N HCl in isopropanol, to remove a BOC group.

The 4-position piperazinyl nitrogen of compound 14 can be alkylated with a compound of formula R$^1$—X in a solvent such as DMF in the presence of Et$_3$N at room temperature, wherein X is —Cl, Br or —I. Techniques for these procedures are well known to those skilled in the art.

The compounds of this invention are also illustrated by the table of Example 3 below.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be sold for these purposes.

The compounds of the present invention are useful in the inhibition of HIV protease the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of a compound of the present invention, or a pharmaceutically acceptable salt thereof.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Dosage levels of the order of 0.02 to 5.0 or 10.0 grams-per-day are useful in the treatment or prevention of the above-indicated conditions, with oral doses two-to-five times higher. For example, infection by HIV is effectively treated by the administration of from 1.0 to 50 milligrams of the compound per kilogram of body weight from one to four times per day. In one preferred regimen, dosages of 100–400 mg every six hours are administered orally to each patient. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention is also directed to combinations of the HIV protease inhibitory compounds with one or more agents useful in the treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

TABLE C

| Drug Name | Manufacturer | Indication |
|---|---|---|
| ANTIVIRALS | | |
| AL-721 | Ethigen (Los Angeles, CA) | ARC, PGL HIV positive, AIDS |
| Recombinant Human Interferon Beta | Triton Biosciences (Almeda, CA) | AIDS, Kaposi's sarcoma, ARC |
| Acemannan | Carrington Labs (Irving, TX) | ARC (See also immunomodulators) |
| Cytovene Ganciclovir | Syntex (Palo Alto, CA) | sight threatening CMV peripheral CMV retinitis |
| d4T Didehydrodeoxy-thymidine | Bristol-Myers (New York, NY) | AIDS, ARC |
| ddI Dideoxyinosine | Bristol-Myers (New York, NY) | AIDS, ARC |
| EL10 | Elan Corp, PLC (Gainesville, GA) | HIV infection (See also immunomodulators) |
| Trisodium Phosphonoformate | Astra Pharm. Products, Inc | CMV retinitis, HIV infection, other CMV infections |
| Dideoxycytidine; ddC | (Westborough, MA) Hoffman-La Roche (Nutley, NJ) | AIDS, ARC |
| Novapren | Novaferon Labs, Inc. (Akron, OH) Diapren, Inc. (Roseville, MN, marketer) | HIV inhibitor |
| Peptide T Octapeptide Sequence | Peninsula Labs (Belmont, CA) | AIDS |
| Zidovudine; AZT | Burroughs Wellcome (Rsch. Triangle Park, NC) | AIDS, adv, ARC pediatric AIDS, Kaposi's sarcoma, asymptomatic HIV infection, less severe HIV disease, neurological involvement, in combination with other therapies. |
| Ansamycin LM 427 | Adria Laboratories (Dublin, OH) Erbamont (Stamford, CT) | ARC |
| Dextran Sulfate | Ueno Fine Chem. Ind. Ltd. (Osaka, Japan) | AIDS, ARC, HIV positive asymptomatic |
| Virazole Ribavirin | Viratek/ICN (Costa Mesa, CA) | asymptomatic HIV positive, LAS, ARC |
| Alpha Interferon | Burroughs Wellcome (Rsch. Triangle Park, NC) | Kaposi's sarcoma, HIV in combination w/Retrovir |
| Acyclovir | Burroughs Wellcome | AIDS, ARC, asymptomatic HIV positive, in combination with AZT. |
| Antibody which neutralizes pH labile alpha aberrant Interferon in an immuno-adsorption column | Advanced Biotherapy Concepts (Rockville, MD) | AIDS, ARC |
| B | Merck (Rahway, NJ) | AIDS, ARC, asymptomatic HIV positive, also in combination with AZT. |
| C | Merck (Rahway, NJ) | AIDS, ARC, asymptomatic HIV positive, also in combination with AZT. |
| Nevirapine | Boehringer Ingelheim | AIDS, ARC, asymptomatic HIV positive, also in combination with AZT. |
| IMMUNO-MODULATORS | | |
| AS-101 | Wyeth-Ayerst Labs. (Philadelphia, PA) | AIDS |
| Bropirimine | Upjohn (Kalamazoo, MI) | advanced AIDS |
| Acemannan | Carrington Labs, Inc. (Irving, TX) | AIDS, ARC (See also anti-virals) |
| CL246,738 | American Cyanamid (Pearl River, NY) Lederle Labs (Wayne, NJ) | AIDS, Kaposi's sarcoma |
| EL10 | Elan Corp, PLC (Gainesville, GA) | HIV infection (See also anti-virals) |
| Gamma Interferon | Genentech (S. San Francisco, CA) | ARC, in combination w/TNF (tumor necrosis factor) |

TABLE C-continued

| Drug Name | Manufacturer | Indication |
|---|---|---|
| Granulocyte Macrophage Colony Stimulating Factor | Genetics Institute (Cambridge, MA) Sandoz (East Hanover, NJ) | AIDS |
| Granulocyte Macrophage Colony Stimulating Factor | Hoeschst-Roussel (Sommerville, NJ) Immunex (Seattle, WA) | AIDS |
| Granulocyte Macrophage Colony Stimulating Factor | Schering-Plough (Madison, NJ) | AIDS AIDS, in combination w/AZT |
| HIV Core Particle Immunostimulant | Rorer (Ft. Washington, PA) | seropositive HIV |
| IL-2 Interleukin-2 | Cetus (Emeryville, CA) | AIDS, in combination w/AZT |
| IL-2 Interleukin-2 | Hoffman-La Roche (Nutley, NJ) Immunex | AIDS, ARC, HIV, in combination w/AZT |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute (Miami, FL) | AIDS, ARC |
| Alpha-2 Interferon | Schering Plough (Madison, NJ) | Kaposi's sarcoma w/AZT: AIDS |
| Methionine-Enkephalin | TNI Pharmaceutical (Chicago, IL) | AIDS, ARC |
| MTP-PE Muramyl-Tripeptide | Ciba-Geigy Corp. (Summit, NJ) | Kaposi's sarcoma |
| Granulocyte Colony Stimulating Factor | Amgen (Thousand Oaks, CA) | AIDS, in combination w/AZT |
| rCD4 Recombinant Soluble Human CD4 | Genentech (S. San Francisco, CA) | AIDS, ARC |
| rCD4-IgG hybrids | | AIDS, ARC |
| Recombinant Soluble Human CD4 | Biogen (Cambridge, MA) | AIDS, ARC |
| Interferon Alfa 2a | Hoffman-La Roche (Nutley, NJ) | Kaposi's sarcoma AIDS, ARC, in combination w/AZT |
| SK&F106528 Soluble T4 | Smith, Kline & French Laboratories (Philadelphia, PA) | HIV infection |
| Thymopentin | Immunobiology Research Institute (Annandale, NJ) | HIV infection |
| Tumor Necrosis Factor; TNF | Genentech (S. San Francisco, CA) | ARC, in combination w/gamma Interferon |
| ANTI-INFECTIVES | | |
| Clindamycin with Primaquine | Upjohn (Kalamazoo, MI) | PCP |
| Fluconazole | Pfizer (New York, NY) | cryptococcal meningitis, candidiasis |
| Pastille Nystatin Pastille | Squibb Corp. (Princeton, NJ) | prevention of oral candidiasis |
| Ornidyl Eflornithine | Merrell Dow (Cincinnati, OH) | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome (Rsch. Triangle Park, NC) | PCP treatment |
| Pentamidine isethionate for inhalation | Fisons Corporation (Bedford, MA) | PCP prophylaxis |
| Spiramycin | Rhone-Poulenc Pharmaceuticals (Princeton, NJ) | cryptosporidial diarrhea |
| Intraconazole-R51211 | Janssen Pharm. (Piscataway, NJ) | histoplasmosis; cryptococcal meningitis |
| Trimetrexate | Warner-Lambert | PCP |
| OTHER | | |
| Recombinant Human Erythropoietin | Ortho Pharm. Corp. (Raritan, NJ) | severe anemia assoc. with AZT therapy |
| Megestrol Acetate | Bristol-Myers (New York, NY) | treatment of anorexia assoc. w/AIDS |
| Total Enteral Nutrition | Norwich Eaton Pharmaceuticals (Norwich, NY) | diarrhea and malabsorption related to AIDS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Certain compounds of Table C are the following: Compound B is 6-chloro-4-(S)-cyclopropyl-3,4-dihydro-4-((2-pyridyl)ethynyl)quinazolin-2(1H)-one; Compound C is(–) 6-chloro-4(S)-trifluoromethyl-1,2-dihydro-4(H)-3,1-benzoxazin-2-one; nevirapine is 11-cyclopropyl-5,11-dihydro-4-methyl-6H-dipyrido[3,2-b:2',3'-e][1,4]diazepin-6-one. Compounds B and C are synthesized by the methods of EP 0,569,083, herein incorporated by reference for this purpose. Nevirapine is synthesized by Klunder, J. M. et al., J. Med. Chem. 35, 1887 (1992); Hargrave, K. D. et al., J. Med Chem. 34, 2231 (1991); Cohen, K. A. et al., J. Biol. Chem. 266, 14670 (1991), all three references herein incorporated by reference.

Preferred combinations are simultaneous or alternating treatments of an inhibitor of HIV protease and a non-nucleoside inhibitor of HIV reverse transcriptase. An optional third component in the combination is a nucleoside inhibitor of HIV reverse transcriptase, such as AZT, ddC or ddI. A preferred inhibitor of HIV protease is Compound A. Preferred non-nucleoside inhibitors of HIV reverse transcriptase include Compound B, Compound C or nevirapine. These combinations may have synergistic effects on limiting the spread of HIV. Preferred combinations include the following (1) Compound A, with a preferred non-nucleoside inhibitor of HIV reverse transcriptase, and, optionally, AZT or ddI or ddC; (2) Compound A, and any of AZT or ddI or ddC.

Assay for Inhibition of Microbial Expressed HIV Protease

Inhibition studies of the reaction of the protease expressed in Eschericia coli with a peptide substrate [Val-Ser-Gln-Asn-(betanapthyl)Ala-Pro-Ile-Val, 0.5 mg/mL at the time the reaction is initiated] were in 50 mM Na acetate, pH 5.5, at 30° C. for 1 hour. Various concentrations of inhibitor in 1.0 $\mu$l DMSO were added to 25 $\mu$l of the peptide solution in water. The reaction is initiated by the addition of 15 $\mu$l of 0.33 nM protease (0.11 ng) in a solution of 0.133M Na acetate pH 5.5 and 0.1% bovine serum albumin. The reaction was quenched with 160 $\mu$l of 5% phosphoric acid. Products of the reaction were separated by HPLC (VYDAC wide pore 5 cm C-18 reverse phase, acetonitrile gradient, 0.1% phosphoric acid). The extent of inhibition of the reaction was determined from the peak heights of the products. HPLC of the products, independently synthesized, proved quantitation standards and confirmation of the product composition. Compound A showed $IC_{50}$ values of about 0.27 nM.

CELL SPREAD ASSAY

Inhibition of the spread of HIV in cell culture was measured according to Nunberg, J. H. et al., J. Virol. 65, 4887 (1991). In this assay, MT-4 T-lymphoid cells were infected with HIV-1 (wild-type, unless otherwise indicated) by using a predetermined inoculum, and cultures were incubated for 24 h. At this time, ≦1% of the cells were positive by indirect immunofluorescence. Cells were then extensively washed and distributed into 96-well culture dishes. Serial twofold dilutions of inhibitor were added to the wells, and cultures were continued for 3 additional days. At 4 days postinfection, 100% of the cells in control cultures were infected. HIV-1 p24 accumulation was directly correlated with virus spread. The cell culture inhibitory concentration was defined as the inhibitor concentration in nanomoles/liter which reduced the spread of infection by at least 95%, or $CIC_{95}$. The $CIC_{95}$ for compound A is 25 nM.

INHIBITION OF VIRUS SPREAD

A. Preparation of HIV-infected MT-4 cell Suspension.

MT cells were infected at Day 0 at a concentration of 250,000 per ml with a 1:1000 dilution of HIV-1 strain IIIb stock (final 125 pg p24/ml; sufficient to yield ≦1% infected cells on day 1 and 25–100% on day 4). Cells were infected and grown in the following medium: RPMI 1640 (Whittaker BioProducts), 10% inactivated fetal bovine serum, 4 mM glutamine (Gibco Labs) and 1:100 Penicillin-Streptomycin (Gibco Labs).

The mixture was incubated overnight at 37° C. in 5% $CO_2$ atmosphere.

B. Treatment with Inhibitors

A matrix of nanomolar range concentrations of the pairwise combinations is prepared. At Day 1, aliquots of 125 μl of inhibitors are added to equal volumes of HIV-infected MT-4 cells (50,000 per well) in a 96-well microtiter cell culture plate. Incubation is continued for 3 days at 37° C. in 5% $CO_2$ atmosphere.

C. Measurement of Virus Spread

Using a multichannel pipettor, the settled cells are resuspended and 125 μl harvested into a separate microtiter plate. The supernatant is assayed for HIV p24 antigen.

The concentration of HIV p24 antigen is measured by an enzyme immunoassay, described as follows. Aliquots of p24 antigen to be measured are added to microwells coated with a monoclonal antibody specific for HIV core antigen. The microwells are washed at this point, and at other appropriate steps that follow. Biotinylated HIV-specific antibody is then added, followed by conjugated streptavidin-horseradish peroxidase. A color reaction occurs from the added hydrogen peroxide and tetramethylbenzidine substrate. Color intensity is proportional to the concentration of HIV p24 antigen.

Calculation of Degree of Synergy or Enhanced Inhibition

When there is synergy pairwise combinations of inhibitors are found to exhibit markedly enhanced inhibition of virus spread, in comparison to each inhibitor alone, or in comparison to merely additive inhibition of each inhibitor.

The data is processed as follows: fractional inhibitory concentration ratios (FIC) are calculated according to Elion, et. al. J. Biol. Chem., 208, 477 (1954). The minimum sum of FICS, which is the maximum synergy, is determined for various pairwise combinations. The smaller the number, the greater the synergy.

EXAMPLE 1

Preparation of N-(2(R)-hydroxy-1(S)-indanyl)-2(R)-phenylmethyl-4(S)-(hydroxy)-5-(1-(2(S)-N-(t-butyl-carboxamido)-piperazinyl)-pentaneamide, Compound 14

Step 1: Preparation of dihydro-5(S)-((t-butyldiphenylsilyl)-oxymethyl)-3(R)phenylmethyl-3(2H)-furanone A solution of lithium diisopropylamide (LDA) was generated by the addition 1.55 ml of n-BuLi (2.5M in hexane) to 0.55 ml (3.9 mmol) of diisopropylamine in 10 ml of THF at −78° C. After 30 minutes a solution of dihydro-5-(S)-((t-butyldiphenylsilyl)-oxymethyl)-3(2H)-furanone (1.38 g, 3.89 mmol) in 5 ml of THF was added. After an additional 30 minutes of stirring, benzyl bromide (0.68 g, 3.9 mmol) was added and stirring was continued for 3 h after which time the reaction was quenched with the addition of a 10% aqueous citric acid solution. The solution was extracted with ethyl acetate (2×50 ml) which was backwashed with brine, dried, filtered and concentrated to afford an oil. The product was purified by chromatography ($SiO_2$, 20% EtOAc/Hexane) to afford the title compound.

Step 2: Preparation of dihydro-5(S)-(hydroxy-methyl)-3(R)-phenylmethyl-3(2H)-furanone To 5.26 g of dihydro-5(S)-((t-butyldiphenylsilyl)oxymethyl)-3(R)phenylmethyl-3(2H)-furanone in 40 ml of acetonitrile was added 1.34 ml of a 49% aqueous HF solution. After 18 hr at room temperature the reaction was concentrated to dryness and the residue was partitioned between water (50 ml) and ethyl acetate (50 ml). The organic layer was washed with brine, dried filtered and concentrated to afford the product as a tan solid (mp 69°–72° C.).

Step 3: Preparation of dihydro-5(S)-((trifluoromethanesulfonyl)-oxvmethyl)-3(R)-phenylmethyl-3(2H)-furanone To a solution of 18.4 g (89.2 mmol) of dihydro-5(S)-(hydroxymethyl)-3(R)-phenylmethyl-3(2H)-furanone in 350 mL of methylene chloride cooled to 0° C. was added 13.51 mL 2,6-lutidine (115.98 mmol) followed by a dropwise addition of 16.51 mL of trifluoromethanesulfonic anhydride (98.1 mmol). After 1.5 hours at 0° C., the reaction was poured into a mixture of 300 mL ice/brine and stirred for 0.5 hours. The aqueous layer was then extracted with methylene chloride (3×150 mL), the organic layers were washed with 10% HCl (2×75 mL), saturated $NaHCO_3$ (100 mL), water (100 mL), dried over $MgSO_4$, filtered and concentrated to give a solid residue. Purification via flash column chromatography (120×150 mm column, gradient elution of hexanes:EtOAc, 4:1 to 3:1) afforded the title product; mp 53°–54° C.

Step 4: Preparation of 4-(1,1-dimethylethoxycarbonylamino)-1-(phenylmethylcarbonylamino)-piperazine-2S-carboxylic acid The title compound was prepared following the procedure of Bigge, C. F.; Hays, S. J.; Novak, P. M.; Drummond, J. T.; Johnson, G.; Bobovski, T. P. Tetrahedron Lett. 1989, 30, 5193; starting with 2(S)-piperazine-carboxylic acid. (see Felder, E.; Maffei, S.; Pietra, S.; Pitre, D.; Helv. Chim. Acta 1960, 117, 888.

Step 5: Preparation of N-t-butyl-4-(1,1-dimethylethoxycarbonyl-amino)-1-(phenylmethylcarbonyl-amino)piperazine-2(S)-carboxamide To 9.90 g (27.16 mmol) of the product of Step 4 dissolved in 75 mL of DMF and cooled to 0° C. was added 5.73 g (29.88 mmol) of EDC, 4.03 g (29.88 mmol) of HOBt, 3.14 mL (29.88 mmol) of t-butylamine, and finally 4.16 mL (29.88 mmol) of triethylamine. The reaction mixture was stirred for 18 hours and the reaction volume was concentrated by half. The mixture was then diluted with 600 mL of EtOAc and washed with 10% HCl (2×75 mL), saturated NaHCO$_3$ (1×75 mL), water (3×75 mL) and brine (1×50 mL), dried over MgSO$_4$ and concentrated to a solid. This solid was triturated with EtOAc: hexane (1:2) and filtered to provide the title product as a white solid; mp 134°–135° C.

Step 6: Preparation of N-t-butyl-4-(1,1-dirnethylethoxycarbonyl-amino)piperazine-2(S)-carboxamide To 1.20 g (2.86 mmol) of N-t-butyl-4-(1,1-dimethylethoxy-carbonylamino)-1-(phenylmethylcarbonyl-amino)piperazine-2(S)-carboxamide and 1.1 g (0.086 mmol) of 10% Pd/C was added 15 mL of methanol. The vessel was charged with hydrogen and the reaction stirred for 2 hours, filtered through celite and washed with ethanol. The solvents were removed in vacuo to provide the title product as a foam.

$^1$H NMR (300 MHz, CDCl$_3$) δ 6.65 (br, 1H), 4.10 (m, 1H), 3.81 (br, 1H), 3.21 (dd, J=18 and 7 Hz, 1H), 3.02–2.70 (m, 4H), 2.10–2.0 (br, 1H), 1.50 (s, 9H), 1.41(s, 9H).

Step 7: Preparation of dihydro-5(S)-(4-(1,1-dimethylethoxy-carbonylamino))-2(S)-N-(t-butylcarboxamido)-piperazinyl)methyl)-3(R)-phenylmethyl-3(2H)-furanone To a solution of 22.40 g (0.0662 mol) dihydro-5(S)-((trifluoromethanesulfonyl)oxymethyl)-3(R)-phenylmethyl-3(2H)-furanone (prep in step 3) and 18.0 g (0.063 mol) of N-t-butyl-4-(1,1-dimethylethoxycarbonylamino)piperazine-2(S)-carboxamide dissolved in 180 mL of isopropanol was added 11.53 mL (0.0662 mol) of N,N-diisopropylethylamine. After 2.5 hours another 1.2 g of dihydro-5(S)-((trifluoromethanesulfonyl)oxymethyl)-3(R)-phenylmethyl-3(2H)-furanone was added. The reaction was complete by thin layer chromatography (TLC) after 3.5 hours and was concentrated to a thick oil. Trituration with EtOAc:hexanes (1:2, 200 mL) provided a white solid which was filtered and discarded. The oil was purified by flash column chromatography (120×150 mm column, EtOAc:hexanes gradient elution 1:1, 2:1, 3:1 to all EtOAc) to afford the title compound.

$^1$H NMR (400 MHz, CDCl$_3$) δ 7.34–7.17 (m, 5H), 6.31 (br s, 1H), 4.38 (br m, 1H), 3.96–3.92 (m, 1H), 3.79 (br m, 1H), 3.16 (dd, J=13.6 and 4.4 Hz, 1H), 3.08–2.99 (m, 3H), 2.90–2.82 (m, 1H), 2.80 (dd, J=13.5 and 8.9 Hz, 1H), 2.78 (m, 1H), 2.67–2.61 (m, 1H), 2.58–2.49 (m, 1H), 2.38–2.32 (m, 1H), 2.32–2.04 (m, 1H), 1.99–1.92 (m, 1H,) 1.45 (s, 9H), 1.29 (s, 9H).

Step 8: Preparation of 2(R)-phenylmethyl-4(S)-(t-butyldimethyl-silyloxy)-5-(1-(4-(1,1-dimethylethoxycarbonylamino)))-2(S)-N-(t-butylcarboxamido)-piperazinyl))-pentaneamide To 25.50 g (52.50 mmol) of dihydro-5(S)-(4-(1,1-dimethyl-ethoxycarbonylamino))-2(S)-N-(t-butylcarboxamido)-piperazinyl)-methyl)-3(R)-phenylmethyl-3(2H)-furanone dissolved in 120 mL DME cooled to 0° C. was added a solution of 60 mL of water and 1.512 g (63.01 mmol) of lithium hydroxide. After 0.5 hours the reaction was quenched with the addition of 10% HCl until pH 6 and the solution was concentrated in vacuo. The residue was dissolved in 50 mL water and extracted with EtOAc (4×75 mL) and the organic layers were washed with water (1×20 mL), brine (1×20 mL). The aqueous was back extracted with EtOAc (2×75 mL) and the combined organic layers were dried over MgSO$_4$ and concentrated to provide a yellow solid. This crude product was dissolved in 100 mL of DMF and 17.87 g (0.262 mol) of imidazole was added, cooled to 0° C. and then 31.50 g (0.21 mol) of t-butyldimethylsilyl chloride was added. This stirred 1 hour at 0° C. and was then warmed to room temperature. After 20 hours the reaction was quenched with 10 mL methanol and concentrated to half the volume. 100 mL of pH 7 buffered water was added and the aqueous was extracted with EtOAc (4×100 mL), the combined organic layers were washed with 10% HCl (2×50 mL), water (3×75 mL), and brine (1×50 mL), dried over MgSO$_4$ and concentrated to obtain the title compound. This material was used directly in the next step.

Step 9: Preparation of N-(2(R)-hydroxy-1(S)-indanyl)-2(R)-phenylmethyl-4(S)-(t-butyldimethylsilyloxy)-5-(1-(4-(1,1-dimethylethoxycarbonylamino)))-2(S)-N-(t-butylcarboxamido)-piperazinyl))-pentaneamide To 27.0 g (0.0446 mol) of the crude material from step 6 dissolved in 180 mL of DMF and cooled to 0° C. was added 8.98 g (0.0468 mol) of EDC, 6.32 g (0.0468 mol) of HOBt, and 7.31 g (0.049 mol) aminohydroxy indane. Triethylamine (6.52 mL, 0.0468 mol) was added and the reaction stirred at 0° C. for 2 hours, room temperature for 16 hours and was quenched by diluting with 500 mL of EtOAc. The organic layer was washed with 10% HCl (2×100 mL), saturated NaHCO$_3$ (1×100 mL), water (3×150 mL), brine (1×75 mL), dried over MgSO$_4$ and concentrated to yield the title compound as a white foam.

$^1$H NMR (400 MHz, CDCl$_3$) δ 7.4–7.17 (m, 9H), 6.51 (br s, 1H), 5.79 (br s, 1H), 5.23 (m, 1H), 4.23 (br s, 1H), 4.06 (m, 1H), 3.96–3.84 (m, 2H), 3.07–2.78 (m, 8H), 3.65 (dd, J=9.6 and 4.1 Hz, 1H), 2.56–2.44 (m, 2H), 2.29 (dd, J=12.0 and 4.5 Hz, 1H), 2.17–2.09 (m, 1H), 1.79 (br s, 1H), 1.44 (s, 9H), 1.35 (s, 9H), 1.10 (s, 1H), 0.84 (s, 9H), 0.12 (s, 3H), 0.08 (s, 3H).

Step 10: Preparation of N-(2(R)-hydroxy-1(S)-indanyl)-2(R)-phenylmethyl-4(S)-(hydroxy)-5-(1-(4-(1,1-dimethylethoxycarbonylamino)))-2(S)-N-(t-butylcarboxamido)-piperazinvl))-pentaneamide To 32.20 g (0.0437 mol) of N-(2(R)-hydroxy-1-(S)-indanyl)-2(R)-phenylmethyl-4(S)-(t-butyldimethylsilyloxy)-5-(1-(4-(1,1-dimethylethoxycarbonylamino)))-2(S)-N-(t-butyl carboxamido)-piperazinyl))-pentaneamide was added 437 mL (0.437 mol) of tetrabutylammonium fluoride (1.0M solution in THF, Aldrich). The reaction stirred for 18 hours and was then concentrated to 200 mL and diluted with 700 mL of EtOAc. This was washed with water (2×100 mL), brine (1×50 mL) and the aqueous layers were back extracted with EtOAc (2×200 mL). The combined organic layers were dried over MgSO$_4$ and concentrated to an oil. Purification via flash column chromatography (120×150 mm column, gradient elution CH$_2$Cl$_2$: CHCl$_3$/saturated with NH$_3$: methanol, increasing methanol from 1%, 1.5%, 2%) afforded the title compound as a white foam.

$^1$H NMR (400 MHz, CDCl$_3$) δ 7.31–7.11 (m, 9H), 6.41 (br s, 1H), 6.23 (d, J=8.6 Hz, 1H), 5.25 (dd, J=8.6 and 4.7 Hz, 1H), 4.21 (m, 1H), 3.83–3.82 (m, 2H), 3.78–3.61 (m, 2H), 3.22–3.19 (m, 2H), 3.03–2.78 (m, 8H), 2.62–2.58 (m, 1H), 2.41–2.35 (m, 2H), 2.04–2.02 (m, 1H), 1.57–1.50 (m, 1H), 1.45 (s, 9H), 1.32 (s, 9H).

Step 11: Preparation of N-(2(R)-hydroxy-1(S)-indanyl)-2(R)-phenylmethyl-4(S)-(hydroxy)-5-(1-(2(S)-N-(t-butylcarboxamido)-piperazinyl)-pentaneamide, Compound 14

To 21.15 g (0.034 mol) of N-(2(R)-hydroxy-1(S)-indanyl)-2(R)-phenylmethyl-4(S)-(hydroxy)-5-(1-(4-(1,1-dimethylethoxy-carbonylamino)))-2(S)-N-(t- butylcarboxamido)-piperazinyl))-pentaneamide dissolved in 350 mL of methylene chloride and cooled to 0° C. was added 22.43 mL (0.204 mol) 2,6-lutidine and then 32.85 mL (0.170 mol) of trimethylsilyltriflate over 5 minutes. After 0.5 hours the reaction was quenched with 10% HCl (80 mL) and this stirred 0.5 hours. To this was added 100 mL of saturated NaHCO₃ and then solid NaHCO₃ until pH 8. The aqueous layer was then extracted with EtOAc (4×100 mL) and the combined organic layers were washed with water (1×50 mL), brine (1×75 mL), dried over MgSO₄ and concentrated. The residue was purified via column chromatography (120× 150 mm column, gradient elution CH₂Cl₂:CHCl₃ saturated with NH₃: MeOH, slowly increasing methanol 2%, 3%, 4%, 5%, 6%, to 10%). This provided the title product as a white foam.

¹H NMR (400 MHz, CDCl₃) δ 7.53 (s, 1H), 7.29–7.09 (m, 9H), 6.52 (d, J=8.3 Hz, 1H), 5.24 (dd, J=8.2 and 4.9 Hz, 1H), 4.23 (dd, J=4.7 and 4.03 Hz, 1H), 4.25–4.00 (br s, 1H), 3.83–3.81 (m, 1H), 3.03–2.88 (m, 4H), 2.82–2.73 (m, 7H), 2.50–1.60 (br s, 2H), 2.45 (d, J=6.2 Hz, 2H), 2.32–2.29 (m, 1H), 1.98 (m, 1H), 1.51 (m, 1H), 1.33 (s, 9H).

EXAMPLE 2

Preparation of N-(2(R)-hydroxy-1(R)-indanyl)-2(R)-phenylmethyl-4(R)-hydroxy-5-(1-(4-(3-furo[2,3-b] pyridylmethyl)-2(R)-N'-(t-butylcarboxamido)-piperazinvl))-pentaneamide Step 1: Preparation of Furo[2,3-b]pyridine-2,5-dicarboxylic acid

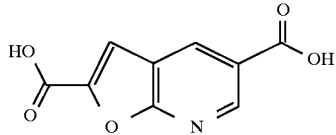

To solution of the known [Snyder, H. R., Ebetino, F. F. *J. Het. Chem.* 3 202–205 (1966)] diethyl furo[2,3-b]pyridine-2,5-dicarboxylate (1.22 g, 4.923 mmol) in 10 mL of 95% ethanol was added a solution of potassium hydroxide (0.66 g, 11.81 mmol) dissolved in 10 mL of water. The reaction was warmed to 80° C. for 3 h, cooled to RT and filtered. The bispotassium salt was dissolved in water and acidified with 10% HCl to pH 2. The precipitate was filtered and dried under vacuum to afford 850 mg of a white solid. ¹H NMR (400 MHz, (CD₃)₂SO) δ 8.98 (d, J=2.2 Hz, 1H), 8.76 (d, J=2.2 Hz, 1H), 7.69 (s, 1H), 4.25 (br s, 3H).

Step 2: Preparation of Furo[2,3-b]pyridine-5-carboxylic acid

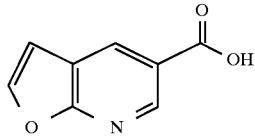

To a suspension of furo[2,3-b]pyridine-2,5-dicarboxylic acid (0.36 g, 1.484 mmol) in 3 mL of quinoline, under Ar, was added Cu powder (180 mg, 2.82 mmol) and warmed to 210° C. for 1.5 h. The reaction was cooled to RT and diluted with 50 mL of methylene chloride and filtered through celite. The organic layer was extracted with sat'd NaCO₃ (2×40 mL), acidified to pH 3 with 3N HCl, and filtered to afford 80 mg of a tan solid. The aqueous layer was extracted with ether/methanol (85/15) (3×50 mL) and washed with brine (1×10 mL), dried over MgSO₄, filtered and concentrated to afford an additional 35 mg of product. ¹H NMR (400 MHz, (CD₃OD) δ 8.89 (s, 1H), 8.67 (d, J=2.0 Hz, 1H), 7.97 (d, J=2.5 Hz, 1H), 7.01 (d, J=2.4 Hz, 1H).

Step 3: Preparation of methyl furo[2.3-b]pyridine-5-carboxylate

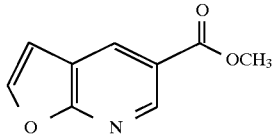

To furo[2,3-b]pyridine-5-carboxylic acid (3.0 g, 18.40 mmol) dissolved in 40 mL of methanol was added 160 mL of chloroform and then trimethysilyldiazomethane (42 mL, 10% solution in hexanes) slowly. After 0.5 h 4 drops glacial acetic acid was added and the reaction mixture was concentrated. This provided 3.20 g as an off white solid. ¹H NMR (400 MHz, CDCl₃) δ 9.02 (d, J=2.0 Hz, 1H), 8.60 (d, J=2.0 Hz, 1H), 7.79 (d, J=2.5 Hz, 1H), 6.87 (d, J=2.5 Hz, 1H), 3.98 (s, 3H).

Step 4: Preparation of 5-hydroxymethyl furo[2,3-b]pyridine

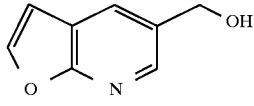

A flame dried 500 mL round bottom flask was charged with methyl furo[2,3-b]pyridine-5-carboxylate (3.20 g, 18.08 mmol) dissolved in 90 mL of THF and cooled to 0° C. To this was added diisobutylaluminum hydride (46 mL, 46.1 mmol, 1M solution in hexanes) over 10 minutes and the cooling bath removed. After 4 h the reaction mixture was cooled to 0° C. and slowly quenched with rochelle salts (100 mL). After an additional 18 h the layers were separated and the aqueous layer was extracted with ethyl acetate (4×40 mL). The combined organic layers were washed with brine (1×20 mL), dried over MgSO₄, filtered and concentrated. The residue was purified via flash column chromatography (40×150 mm column, gradient elution CH₂Cl₂:CH₂Cl₂ sat'd with NH₃: MeOH 60:39:1.0 (1000 mL), 60:38:2 (1000 mL), 60:37:3 (1000 mL), 60:36:4 (1000 mL). This provided 2.16 g of a white solid. ¹H NMR (400 MHz, CDCl₃) δ 8.19 (d, J=2.0 Hz, 1H), 7.92 (d, J=2.0 Hz, 1H), 7.64 (d, J=2.5 Hz, 1H). 6.69 (d, J=2.4 Hz, 1H), 4.78 (d, J=3.8 Hz, 2H), 4.69 (br s, 1H).

Step 5: Preparation of 3-chloromethyl furo[2,3-b]pyridine hydrochloride

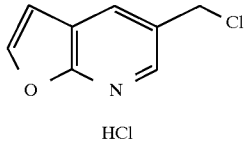

HCl

To a solution of 5-hydroxymethyl furo[2,3-b]pyridine dissolved in 9 mL of methylene chloride cooled to 0° C. was added thionyl chloride (4.23 mL, 57.99 mmol). The ice bath was removed and after 1 h the reaction mixture was concentrated to afford 2.86 g of an off white solid. ¹H NMR (400 MHz, CDCl₃) δ 8.40 (d, J=2.0 Hz, 1H), 8.13 (d, J=2.2 Hz, 1H), 7.80 (d, J=2.4 Hz, 1H), 6.86 (d, J=2.4 Hz, 1H), 4.74 (s, 2H).

Step 6: Preparation of N-(2(R)-hydroxy-1(S)-indanyl)-2(R)-phenylmethyl-4(S)-hydroxy-5-(1-(4-(3-furo[2,3-b]- pyridylmethyl)-2(S)-N'-(t-butylcarboxamido)-piperazinyl))-pentaneamide

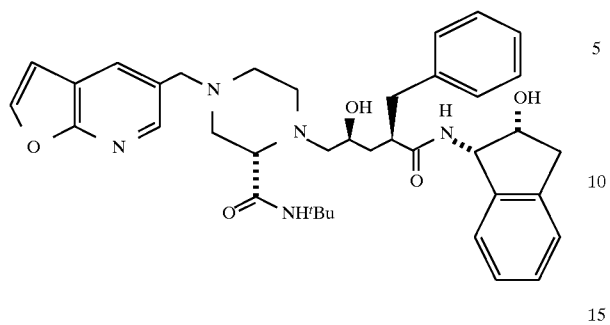

To a solution of N-(2(R)-hydroxy-1(S)-indanyl)-2(R)-phenylmethyl-4(S)-hydroxy-5(-2(S)-N'-(t-butylcarboxamido)-piperazinyl))pentaneamide (6.50 g, 12.48 mmol) dissolved in 12 mL of dimethylfornamide, under argon, was added 3-chloromethylfuro[2,3-b]pyridine hydrochloride (2.80 g, 13.72 mmol) and triethylamine (5.21 mL, 37.44 mmol). After 18 h the reaction mixture was diluted with 400 mL of ethyl acetate and washed with sat'd $NaHCO_3$ (1×25 mL), water (5×20 mL), and brine (1×25 mL). The solution was dried over $MgSO_4$, filtered and concentrated to an oil. The residue was purified via flash column chromatography (60×150 mm column, gradient elution $CH_2Cl_2$:$CH_2Cl_2$ sat'd with $NH_3$: MeOH 60:39:1.0 (1000 mL), 60:38:2 (1500 mL), 60:37:3 (1500 mL), 60:36:4 (1500 mL). Titrated the resulting foam in ethyl acetate and the desired product was filtered and dried overnight under high vacuum at 65° C. to provide 5.30 g of white crystalline solid. Mixed fractions from the column chromatography could be combined and repurified to afford more product. mp 183.5–184.5° C. $^1$H NMR (400 MHz, $CDCl_3$) δ 8.25 (d, J=2.2 Hz, 1H), 7.85 (d, J=2.0 Hz, 1H), 7.75 (s, 1H), 7.73 (d, J=2.4 Hz, 1H), 7.32–7.10 (m, 9H), 6.75 (d, J=2.4 Hz, 1H), 5.95 (d, J=8.6 Hz, 1H), 5.27 (dd, J=8.5, and 4.8 Hz, 1H), 4.27–4.26 (m, 1H), 4.12 (br s, 1H), 3.89–3.83 (m, 1H), 3.51 (s, 2H), 3.29 (dd, J=17.5 and 4.0 Hz, 1H), 3.16 (dd, J=3.66 and 3.48 Hz, 1H), 3.15 (dd, J=6.6 and 5.1 Hz, 1H), 2.94–2.50 (m, 11H), 2.36–2.34 (m, 1H), 1.66 (s, 1H), 1.62–1.47 (m, 1H), 1.35 (s, 9H).

Analysis calculated for $C_{38}H_{47}N_5O_5$ C, 69.81; H, 7.25; N, 10.71; Found: C, 69.46; H, 7.22; N, 10.69

EXAMPLE 3

Employing substantially the same procedure as described in Example 2, but treating the N-(2(R)-hydroxy-1(S)-indanyl)-2(R)-phenylmethyl-4(S)-hydroxy-5-(1-(2(S)-N'-(t-butylcarboxamido)-piperazinyl))-pentaneamide used therein (compound (i) below) with the alkylating agent (ii) indicated below in place of the alkylating agent used in Step 6 therein, the following products defined by formula (iii) were made:

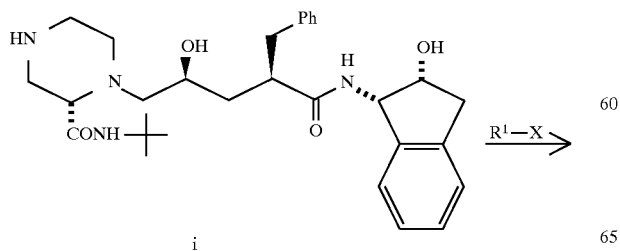

i

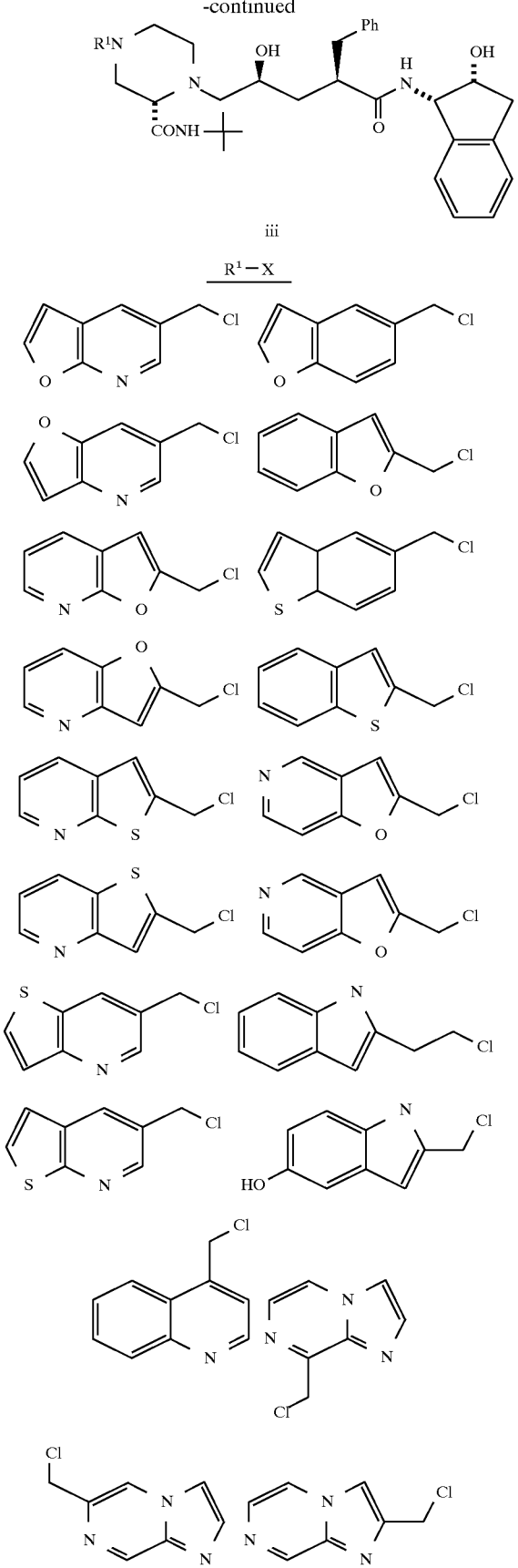

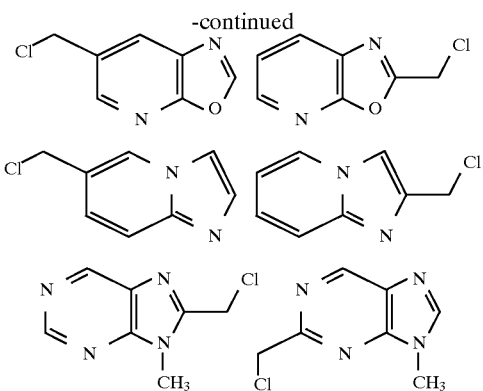

EXAMPLE 4
Preparation of Amide 1

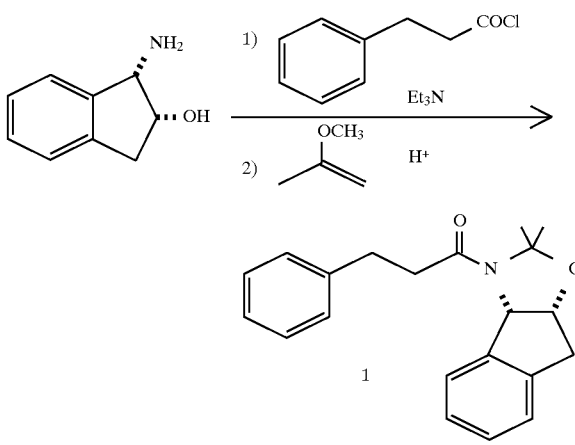

A solution of (−)-cis-1-aminoindan-2-ol (884 g, 5.93 mol) in 17.8 L of dry THF (KF=55 mg/mL) (KF stands for Karl Fisher titration for water) and triethylamine (868 mL, 6.22 mol) in a 50 L round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over 75 minutes, while the internal temperature was kept between 14°–24° C. with an ice-water cooling batch. After addition, the mixture was aged at 18° to 20° C. for 30 minutes and checked by HPLC analysis for the disappearance of (−)-cis-1-aminoindan-2-ol.

Progress of the reaction is monitored by high performance liquid chromatography (HPLC) analysis: 25 cm Dupont C8-RX column, 60:40 acetonitrile/10 mM ($KH_2PO_4$/$K_2HPO_4$), 1.0 mL/min., injection volume=20 mL, detection=200 nm, sample preparation=500×dilution. Approximate retention times:

| retention time (min.) | identity |
| --- | --- |
| 6.3 | cis-aminoindanol |

The reaction was treated with pyridinium p-toluenesulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h. The reaction mixture was cooled to 20° C. and partitioned with ethyl acetate (12 L) and 5% aqueous $NaHCO_3$ (10 L). The mixture was agitated and the layers were separated. The ethyl acetate extract was washed with 5% aqueous $NaHCO_3$ (10 L) and water (4 L). The ethyl acetate extract was dried by atmospheric distillation and solvent switched to cyclohexane (total volume of ~30 L). At the end of the distillation and concentration (20 volume % of ethyl acetate extraction volume), the hot cyclohexane solution was allowed to slowly cool to 25° C. to crystallize the product. The resulting slurry was further cooled to 10° C. and aged for 1 h. The product was isolated by filtration and the wet cake was washed with cold (10° C.) cyclohexane (2×800 mL). The washed cake was dried under vacuum (26" of Hg) at 40° C. to afford 1.65 kg of acetonide 1 (86.4%, 98 area % by HPLC), $^1$H NMR (300.13 MHz, $CDCl_3$, major rotamer) δ 7.36–7.14 (m, 9H), 5.03 (d, J=4.4, 1H), 4.66 (m, 1H) 3.15 (m, 2H), 3.06 (br s, 2H), 2.97 (m, 2H), 1.62 (s, 3H), 1.37 (s, 3H); $^{13}$C NMR (75.5 MHz, $CDCL_3$, major rotamer) $δ_c$ 168.8, 140.9, 140.8, 140.6, 128.6, 128.5, 128.4, 127.1, 126.3, 125.8, 124.1, 96.5, 78.6, 65.9, 38.4, 36.2, 31.9, 26.5, 24.1. Anal. Calcd for $C_{21}H_{23}NO_2$: C, 78.47; H, 7.21; N, 4.36. Found: C, 78.65; H, 7.24; N, 4.40.

EXAMPLE 5
Preparation of Epoxide 3

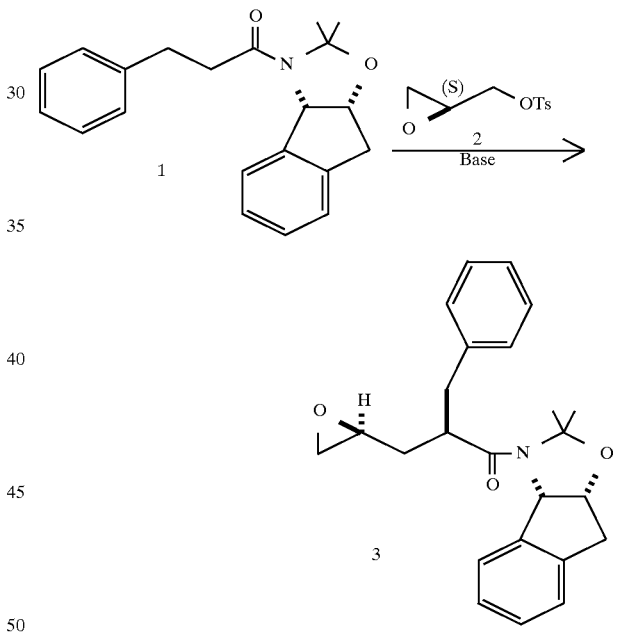

A solution of acetonide 1 (1000 g, 3.11 mol) and 2(S)-glycidyl tosylate 2 (853 g, 3.74 mol, 1.2 equiv.) in 15.6 L of THF (KF=22 mg/mL) in a 50 L 4-neck round bottom flask, equipped with a thermocouple, mechanical stirrer, addition funnel and nitrogen inlet adapter was degassed 3 times via vacuum-nitrogen purge and cooled to −56° C. Then, lithium hexamethyldisilazide ($LiN[(CH_3)_3Si]_2$)(2.6 L, 1.38M, 1.15 equiv.) was added over 2 h, while keeping the internal temperature between −50° to −45° C. The reaction mixture was stirred at −45° to −40° C. for 1 h and then allowed to warm to −25° C. over 1 h. The mixture is stirred between −25° to −22° C. for 4 h (or until the starting acetonide is 3.0 area %).

Progress of the reaction is monitored by HPLC analysis: 25 cm×4.6 nm Zorbax Silica column, 20% ethyl acetate in hexane, 2.0 mL/min, injection volume=20 mL, detection=

254 nm, sample preparation=100×dilution. Approximate retention times:

| retention time (min.) | identity |
|---|---|
| 5.5 | amide 1 |
| 6.5 | glycidyl tosylate 2 |
| 13.5 | epoxide 3 |

The reaction mixture was quenched with DI water (6.7 L) at −15° C. and partitioned with ethyl acetate (10 L). The mixture was agitated and the layers were separated. The ethyl acetate extract was washed with a mixture of 1% aqueous NaHCO$_3$ (5 L) and saturated NaCl (0.5 L). The ethyl acetate extract (28.3 L) was concentrated by vacuum distillation (28" of Hg) and additional ethyl acetate was added to complete the solvent switch to ethyl acetate (final volume=11.7 L). The ethyl acetate concentrate was further solvent switched to MeOH to crystallize the product and concentrated to a final volume of 3.2 L. The residual ethyl acetate solvent was removed by charging 10 L of methanol and collecting 10 L of distillate. The resulting slurry was stirred at 22° C. for 1 h, then cooled to 5° C. and aged for 0.5 h. The product was isolated by filtration and the wet cake was washed with cold methanol (2×250 mL). The washed cake was dried under vacuum (26" of Hg) at 25° C. to afford 727 g of epoxide 3 (61.2%, 98.7 area % of the major epoxide by HPLC): $^{13}$C NMR (300 MHz, CDCL$_3$) δ 171.1, 140.6, 140.5, 139.6, 129.6, 128.8, 128.2, 127.2, 126.8, 125.6, 124.1, 96.8, 79.2, 65.8, 50.0, 48.0, 44.8, 39.2, 37.4, 36.2, 26.6, 24.1.

EXAMPLE 6

Preparation of penultimate 6

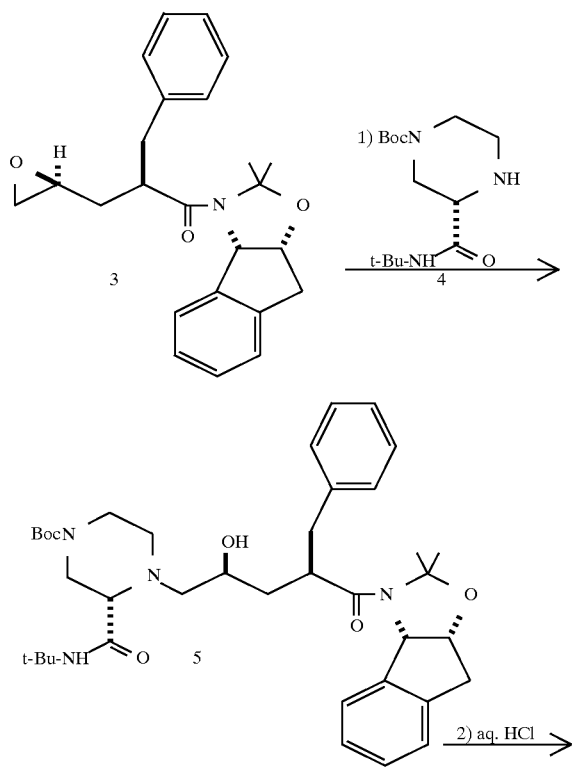

-continued

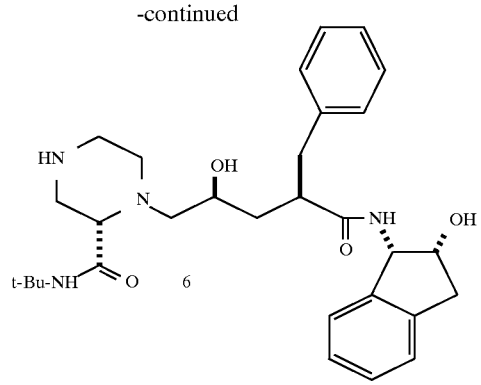

A slurry of the 2(S)-t-butylcarboxarnide-4-N-Boc-piperazine 4 (1950 g, 6.83 mol, >99.5% ee) (ee=enantiomeric excess) and the epoxide 3 (2456 g, 97.5:2.5 mixture of 4S/R epoxides, 6.51 mol) in isopropanol (2-propanol, 18.6 L) in a 72 L round bottom flask with four inlets, equipped with a mechanical stirrer, reflux condenser, steam bath, Teflon coated thermocouple and nitrogen inlet, was heated to reflux (internal temperature was 84°–85° C.). After 40 min, a homogeneous solution was obtained. The mixture was heated at reflux for 28 h.

The internal temperature during reflux was 84°–85° C. Progress of the reaction was monitored by HPLC analysis: 25 cm Dupont C8-RX column, 60:40 acetonitrile/10 mM (KH$_2$PO$_4$/K$_2$HPO$_4$), 1.0 mL/min., detection=220 nm, sample preparation=2 μL, reaction mixture diluted to 1 mL in acetonitrile. Approximate retention times:

| retention time (min) | identity |
|---|---|
| 4.8 | piperazine 4 |
| 8.9 | epoxide 3 |
| 15.2 | coupled product 5 |

After 28 h, the remaining epoxide 3 and coupled product 5 (by HPLC analysis) were 1.5 area % and 91–93 area %, respectively. The mixture was cooled to 0° to 5° C. and 20.9 L of 6N HCl was added while keeping the temperature below 15° C. After the addition was complete, the mixture was warmed to 22° C. Evolution of gas is noted at this point (isobutylene). The mixture was aged at 20° to 22° C. for 6 h.

Progress of the reaction was monitored by HPLC analysis: same conditions as above. Approximate retention times:

| retention time (min) | identity |
|---|---|
| 7.0 | cis-aminoindanol |
| 11.9 | penultimate 6 |
| 15.1 | coupled product 5 |

The mixture was cooled to 0° C. and 7.5 L of 50% NaOH was slowly added to adjust the pH of the mixture to pH=11.6, while keeping the temperature less than 25° C. during the addition. The mixture was partitioned with ethyl acetate (40 L) and water (3 L). The mixture was agitated and the layers were separated. The organic phase (60 L) was concentrated under reduced pressure (29" of Hg) and solvent switched to DMF and concentrated to a final volume of 10.5 L (KF=1.8 mg/mL). The HPLC assay yield of 6 in ethyl acetate was 86.5%. The penultimate compound 6 in DMF was directly used in the next step without further purification. For isolated 6: $^{13}$C NMR (75.4 MHz, CDCl$_3$) δ 175.2, 170.5, 140.8, 140.5, 139.9, 129.1, 128.5, 127.9, 126.8, 126.5, 125.2, 124.2, 73.0, 66.0, 64.8, 62.2, 57.5, 49.5, 47.9, 46.4, 45.3, 39.6, 39.3, 38.2, 28.9.

EXAMPLE 7
Pyrazine-2-tert-butyl carboxamide 9

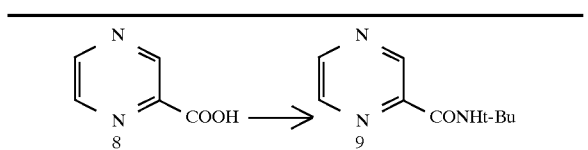

| 2-Pyrazinecarboxylic acid (8) | 3.35 kg (27 mol) |
| Oxalyl chloride | 3.46 kg (27.2 mol) |
| tert-Butylamine (KF = 460 μg/ml) | 9.36 L (89 mol) |
| EtOAc (KF = 56 μg/ml) | 27 L |
| DMF | 120 mL |
| 1-Propanol | 30 L |

The carboxylic acid 8 was suspended in 27 L of EtOAc and 120 mL of DMF in a 72 L 3-neck flask with mechanical stirring under N$_2$ and the suspension was cooled to 2° C. The oxalyl chloride was added, maintaining the temperature between 5° and 8° C.

The addition was completed in 5h. During the exothermic addition CO and CO$_2$ were evolved. The HCl that was formed remained largely in solution. A precipitate was present which is probably the HCL salt of the pyrazine acid chloride. Assay of the acid chloride formation was carried out by quenching an anhydrous sample of the reaction with t-butylamine. At completion <0.7% of acid 8 remained.

The assay for completion of the acid chloride formation is important because incomplete reaction leads to formation of a bis-tert-butyl oxamide impurity.

The reaction can be monitored by HPLC: 25 cm Dupont Zorbax RXC8 column with 1 mL/min flow and detection at 250 nm; linear gradient from 98% of 0.1% aqueous H$_3$PO$_4$ and 2% CH$_3$CN to 50% aqueous H$_3$PO$_4$ and 50% CH$_3$CN at 30 min. Retention times: acid 8=10.7 min, amide 9=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% NaHCO$_3$ and 2×2 L of saturated aq. NaCl. The organic phase was treated with 200 g of Darco G60 carbon and filtered through Solka Flok and the cake was washed with 4 L of EtOAc.

Carbon treatment efficiently removed some purple color in the product.

The EtOAc solution of 9 was concentrated at 10 mbar to 25% of the original volume. 30 L of 1-propanol were added, and the distillation was continued until a final volume of 20 L was reached.

At this point, the EtOAc was below the limit of detection in the $^1$H NMR (<1%). The internal temperature in this solvent change was <30° C. A 1-propanol/EtOAC solution of 3 was stable to reflux atatmospheric pressure for several days.

Evaporation of an aliquot gave a tan solid m.p 87°–88° C. $^{13}$C NMR (75 MHz, CDCl$_3$, ppm) 161.8, 146.8, 145.0, 143.8, 142.1, 51.0, 28.5.

EXAMPLE 8
rac-2-tert-Butyl-carboxamide-piplerazine 10

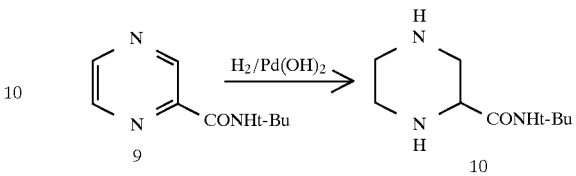

Materials

Pyrazine-2-tert-butylcarboxamide 9 2.4 kg (13.4 mol) in 1-Propanol solution 12 L 20% Pd(OH)$_2$/C 16 wt. % water 144 g.

The pyrazine-2-tert-butylcarboxamide 9/1-propanol solution was placed into the 5 gal autoclave. The catalyst was added and the mixture was hydrogenated at 65° C. at 40 psi (3 atm) of H$_2$.

After 24 h. the reaction had taken up the theoretical amount of hydrogen and GC indicated <1% of 9. The mixture was cooled, purged with N$_2$ and the catalyst was removed by filtration through Solka Floc. The catalyst was washed with 2 L of warm 1-propanol.

It was found that the use of warm 1-propanol during washing of the filter cake improved filtration and lowered the losses of product on the filter cake.

The reaction was monitored by GC: 30 m Megabore column, from 100° C. to 160° C. at 10° C./min, hold 5 min, then at 10° C./min to 250° C., retention times: 9=7.0 min, 10=9.4 min. The reaction could also be monitored by TLC with EtOAc/MeOH (50:50) as solvent and Ninhydrin as developing agent.

Evaporation of an aliquot indicated that the yield over amidation and hydrogenation is 88% and that the concentration of 10 is 133 g/L.

Evaporation of an aliquot gave 10 as a white solid m.p. 150°–151° C.; $^{13}$C NMR (75 MHz, D$_2$O, ppm) 173.5, 59.8, 52.0, 48.7, 45.0, 44.8, 28.7.

EXAMPLE 9
(S)-2-tert-Butyl-carboxamide-piperazine bis (S)-Camphorsulfonic acid salt (S)-11

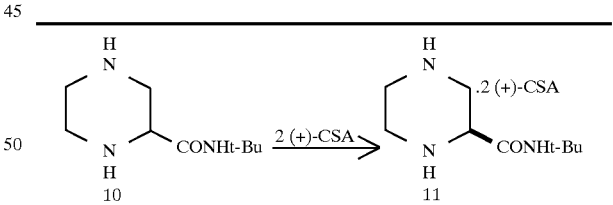

Materials

| rac-2-tert-Butyl-carboxamide-piperazine 10 in 1-Propanol Solution | 4.10 kg (22.12 mol) in 25.5 Kg solvent |
| (S)-(+)-10-Camphorsulfonic acid | 10.0 Kg (43.2 mol) |
| 1-Propanol | 12 L |
| Acetonitrile | 39 L |
| Water | 2.4 L |

The solution of amine 10 in 1-propanol was charged to a 100 L flask with an attached batch concentrator. The solution was concentrated at 10 mbar and a temperature<25° C. to a volume of ca 12 L.

At this point the product had precipitated from the solution, but went back into a solution when the mixture was heated to 50° C.

Analysis of a homogeneous aliquot indicated that the concentration of 10 was 341 g/L The concentration was determined by HPLC: 25 cm Dupont Zorbax RXC8 column with 1.5 mL/min flow and detection at 210 nm, isocratic (98/2) $CH_3CN/0.1\%$ aqueous $H_3PO_4$. Retention time of 10:2.5 min.

Acetonitrile (39 L) and water (2.4 L) were added to give a clear, slightly brown solution.

Determination of the water content by KF titration and $CH_3CN$/1-propanol ratio by $^1H$ NMR integration showed that the CH3CN/1-propanol/$H_2O$ ratio was 26/8/1.6. The concentration in the solution was 72.2 g/L.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21° C. over 8 h.

The product precipitated at 62° C. The product was filtered without aging at 21° C., and the filter cake was washed with 5 L of the $CH_3CN$/1-propanol/$H_2O$ 26/8/1.6 solvent mixture. It was dried at 35° C. in the vacuum oven with $N_2$ bleed to give 5.6 Kg (39%) of 11 as a white crystalline solid m.p 288°–290° C. (with decomp.) $[\alpha]D^{25}=18.9°$ (c=0.37, $H_2O$). $^{13}C$ NMR (75 MHz, $D_2O$, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The ee of the material was 95% according to the following chiral HPLC assay: an aliquot of 11 (33 mg) was suspended in 4 mL of EtOH and 1 mL of $Et_3N$. $Boc_2O$ (11 mg) was added and the reaction mixture was allowed to age for 1 h. The solvent was completely removed in vacuo, and the residue was dissolved in ca. 1 mL of EtOAc and filtered through a Pasteur pipet with $SiO_2$, using EtOAc as eluent. The evaporated product fractions were redissolved in hexanes at ca. 1 mg/mL. The enantiomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 10
(S)-2-tert-Butylcarboxamide-4-tert-butoxycarbonyl-piperazine 4 from salt 11

| | |
|---|---|
| H<br>N<br>⟨ ⟩.2 (+)-CSA<br>N CONHt-Bu<br>H<br>11 | Boc<br>N<br>⟨ S⟩<br>N CONHt-Bu<br>H<br>4 |

$(Boc)_2O$ →

Materials

| | |
|---|---|
| (S)-2-tert-Butyl-carboxamide-piperazine Bis (S)-(+)-CSA salt 11, 95% ee | 5.54 Kg (8.53 mol) |
| Di-tert-butyl dicarbonate | 1.86 Kg (8.53 mol) |
| $Et_3N$ | 5.95 L (42.6 mol) |
| EtOH Punctilious 200 proof | 55 L |
| EtOAc | 2 L |

To the (S)-CSA salt 11 in a 100 L 3-neck flask with an addition funnel under $N_2$ was added EtOH, followed by triethylamine at 25° C. The solid dissolved readily on the addition of the $Et_3N$. The $Boc_2O$ was dissolved in EtOAc and charged to the addition funnel. The solution of $Boc_2O$ in EtOAc was added at such a rate as to keep the temperature below 25° C. The addition took 3 h. The reaction mixture was aged for 1 h after completion of the addition of the $Boc_2O$ solution.

The reaction can be monitored by HPLC: 25 cm Dupont Zorbax RXC8 column with 1 mL/min flow and detection at 228 nm, isocratic (50/50) $CH_3CN/0.1M$ $KH_2PO_4$ adjusted to pH=6.8 with NaOH. Retention time of 4=7.2 min. The chiral assay was carried out using the same system as in the previous step. The reaction could also be monitored by TLC with a 100% EtOAc as the solvent. ($R_f$=0.7)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous $Na_2CO_3$ solution, 2×10 L Di water and 2×6 L of saturated aqueous sodium chloride. The combined aqueous washes were back extracted with 20 L of EtOAc and the organic phase was washed with 2×3 L water and 2×4 L of saturated aqueous sodium chloride. The combined EtOAc extracts were concentrated under 10 mbar vacuum with an internal temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything went into solution. The solution was cooled and seed (10 g) was added at 58° C. The slurry was cooled to 22° C. in 4 h and the product was isolated by filtration after a 1 h age at 22° C. The filter cake was washed with 1.8 L of cyclohexane and dried in the vacuum oven at 35° C. under $N_2$ bleed to give 1.87 Kg (77%, >99.9 area % by HPLC, R-isomer below level of detection) of 4 as a slightly tan powder. $[\alpha]D^{25}=22.0°$ (c=0.20, MeOH), m.p 107° C.; $^{13}C$ NMR (75 MHz, $CDCl_3$, ppm) 170.1, 154.5, 79.8, 58.7, 50.6, 46.6, 43.6, 43.4, 28.6, 28.3.

While the foregoing specification teaches the principles of the present invention, with examples provided for the purpose of illustration, it will be understood that the practice of the invention emcompasses all of the usual variations, adaptations, or modifications, as come within the scope of the following claims and its equivalents.

What is claimed is:

1. A combination of compounds comprising effective amounts of a compound of the formula:

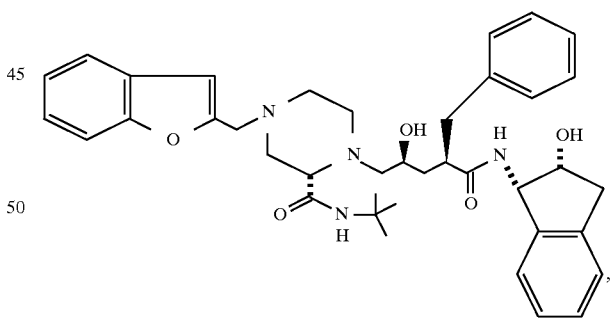

or a pharmaceutically acceptable salt thereof, and one or more nucleoside reverse transcriptase inhibitors selected from AZT, ddI or ddC.

2. A method of treating AIDS comprising administering to a mammal in need of such treatment an effective amount of the combination of claim 1.

3. A method of treating infection by HIV comprising administering to a mammal in need of such treatment an effective amount of the combination of claim 1.

* * * * *